United States Patent [19]
Au-Young et al.

[11] Patent Number: 5,734,038
[45] Date of Patent: Mar. 31, 1998

[54] HUMAN DBI/ACBP-LIKE PROTEIN

[75] Inventors: Janice Au-Young, Berkeley; Jennifer L. Hillman, San Jose; Surya K. Goli, Sunnyvale, all of Calif.

[73] Assignee: Incyte Pharmaceuticals, Inc., Palo Alto, Calif.

[21] Appl. No.: 700,626

[22] Filed: Aug. 16, 1996

[51] Int. Cl.$^6$ .................. C12N 15/00; C12N 1/20; C12P 21/06; C07H 21/04
[52] U.S. Cl. ............... 536/23.5; 435/320.1; 435/252.33; 435/69.3
[58] Field of Search ............ 536/23.5; 435/320.1, 435/252.33, 69.3

[56] References Cited

PUBLICATIONS

Guidotti, A et al., "Isolation, characterization, and purification to homogeneity of an endogenous polypeptide with agonistic action on benzodiazepine receptors" *Proc Nat Acad Sci USA* 80:3531–3535 (1983).

Mikkelsen, J et al., "Amino acid sequence of acyl–CoA–binding protein from cow liver" *Biochem J* 245:857–861 (1987).

Knudsen, J et al., The function of acyl–CoA–binding protein (ACBP)/Diazepam binding inhibitor (DBI) *Mol Cell Biochem* 123:129–138 (1993).

Andersen, KV and Poulsen, FM, "Three–dimensional structure in solution of acyl–coenzyme A binding protein from bovine liver" *J Mol Biol* 226:1131–41 (1992).

Kragelund, BB et al., "Three–dimensional Structure of the Complex between Acyl–Coenzyme A Binding Protein and Palmitoyl–Coenzyme A" *J Mol Biol* 230:1260–1277 (1993).

Rosendal, J et al., "Characterization of ligand binding to acyl–CoA–binding protein" *Biochem J* 290:321–326 (1993).

Rasmussen, JT et al., "Acyl–CoA–binding protein (ACBP) can mediate intermembrane acyl–CoA transport and donate acyl–CoA for beta–oxidation and glycerolipid synthesis" *Biochem J* 299:165–170 (1994).

Alho, H et al., "Increased Expression of Diazepam Binding Inhibitor in Human Brain Tumors" *Cell Growth Differ* 6:309–314 (1995).

Costa, E and Guidotti, A, "Diazepam binding inhibitor (DBI): a peptide with multiple biological actions" *Life Sciences* 49(5):325–344 (1991).

Garnier, M et al., "Diazepam binding inhibitor is a paracrine/autocrine regulator of Leydig cell proliferation and steroidogenesis: action via peripheral–type benzodiazepine receptor and independent mechanisms" *Endocrinology* 132(1):444–458 (1993).

Yanagibashi, K et al., "The Regulation of Intracellular Transport of Cholesterol in Bovine Adrenal Cells: Purificaiton of a Novel Protein" *Endocrinology* 123(4):2075–2082 (1988).

Boujrad, N et al., "Inhibition of hormone–stimulated steroidogenesis in cultured Leydig tumor cells by a cholesterol–linked phosphorothioate oligodeoxynucleotide antisense to diazepam–binding inhibitor" *Proc Nat Acad Sci USA* 90:5728–5731 (1993).

Bovolin, P et al., "Distribution and characterization of diazepam binding inhibitor (DBI) in peripheral tissues of rat" *Reg Peptides* 29:267–281 (1990).

Gray, PW et al., "Cloning and expression of cDNA for human diazepam binding inhibitor, a natural ligand of an allosteric regulatory site of the γ–aminobutyric acid type A receptor" *Proc Nat Sci USA* 83:7547–7551 (1986) (Accession GI 181478).

Marquardt, H et al., "Diazepam binding inhibitor is a paracrine/autocrine regulator of Leydig cell proliferation and steroidogenesis: action via peripheral–type benzodiazepune receptor and independent mechanisms" *J Biol Chem* 261(21):9727–9731 (1986) (Accession GI 118276).

*Primary Examiner*—Christina Y. Chan
*Assistant Examiner*—Patrick Nolan
*Attorney, Agent, or Firm*—Incyte Pharmaceuticals; Lucy J. Billings

[57] ABSTRACT

The present invention provides polynucleotides which identify and encode a novel human Diazepam binding inhibitor/acyl-CoA binding protein (DBI/ACBP)-like protein (DBIH). The invention provides for genetically engineered expression vectors and host cells comprising the nucleic acid sequence encoding DBIH. The invention also provides for the use of substantially purified DBIH for drug delivery as well as for the production of recombinant proteins for the treatment of diseases associated with the expression of DBIH. Additionally, the invention provides for the use of antisense molecules to DBIH in the treatment of diseases associated with the expression of DBIH. The invention also describes diagnostic assays which utilize diagnostic compositions comprising the polynucleotides which hybridize with naturally occurring sequences encoding DBIH and antibodies which specifically bind to the protein.

6 Claims, 7 Drawing Sheets

```
                                                                              54
5' TTG GGT CCG ACT GGA GCT CAG GCT CCA CGC GAC CCA GAC TGG TGG GCC AGG CCT CCA

108
AGC CGG CCT TAC ACC CAA TCC AAG GAG GAC AGA CCG GAC AGA GAG GGA CGG AGC

162
GAG CAA GGA GAC ATG GCT TCA TCA TTC CTG CCC GCG GGG GCC ATC ACC GGC GAC
             M   A   S   S   F   L   P   A   G   A   I   T   G   D

216
AGC GGT GAG GAG CTG AGC TCA GGG GAC GAC TCC GGG GAG GTG GAG TTC CCC CAT
 S   G   E   L   S   S   G   D   D   S   G   E   V   E   F   P   H

270
AGC CCT GAG ATC GAG GAG ACC AGT TGC CTG GCC GAG CTG TTT GAG AAG GCT GCC
 S   P   E   I   E   E   T   S   C   L   A   E   L   F   E   K   A   A

324
GCG CAC CTG CAA GGC CTG ATT CAG GTG GCC AGG GAG CAG CTC TTG TAC CTG
 A   H   L   Q   G   L   I   Q   V   A   S   R   E   Q   L   L   Y   L

378
TAT GCC AGG TAC AAA CAG GTC AAA GTT GGA AAT TGT AAT ACT CCT AAA CCA AGC
 Y   A   R   Y   K   Q   V   K   V   G   N   C   N   T   P   K   P   S
```

FIGURE 1A

```
              387         396         405         414         423         432
TTC TTT GAT TTT GAA GGA AAG CAA AAA TGG GAA GCT TGG AAA GCA CTT GGT GAT
 F   F   D   F   E   G   K   Q   K   W   E   A   W   K   A   L   G   D 441         450         459         468         477         486
TCA AGC CCC AGC CAA GCA ATG CAG GAA TAT ATC GCA GTA GTT AAA AAA CTA GAT
 S   S   P   S   Q   A   M   Q   E   Y   I   A   V   V   K   K   L   D 495         504         513         522         531         540
CCA GGT TGG AAT CCT CAG ATA CCA GAG AAG AAA CGG AAA AGA AGC AAA TAC AAG
 P   G   W   N   P   Q   I   P   E   K   K   R   K   R   S   K   Y   K 549         558         567         576         585         594
GTT TGG GCC AGT TAT TAG TTC TCT ATA TCA TGA AGA AAC CAT CAG GGA AGA GAC
 V   W   A   S   Y   *

603         612         621         630         639         648
AAA AAT ATA TTT GAT TAC TGC AGG GAA AAC AAC ATT GAC CAT ATA ACC AAA GCC 657         666         675         684         693         702
ATC AAA TCG AAA AAT GTG GAT GTG AAT GAT GAA GAG GGT AGG GCT CTA 711         720         729         738         747         756
CTT CAC TGG GCC TGT GAT CGA GGA CAT AAG GAA CTA GTC ACA GTG TTG CTG CAA
```

FIGURE 1B

```
              765        774         783         792         801         810
         CAT AGA GCT GAC ATT AAC TGT CAG GAC AAT GAA GGC CAA ACA GCT CTA CAT TAT 819        828         837         846         855         864
         GCC TCT GCC TGT GAG TTT CTG GAT ATT GTA GAG CTG CTC CAG TCT GGT GCT 873        882         891         900         909         918
         GAC CCC ACT CTC CGA GAC CAG GAT GGC TGC CTG CCA GAG GAG GTG ACA GGC TGC 927        936         945         954         963         972
         AAA ACA GTT TCT TTG GTG CTG CAG CGG CAC ACA ACT GGC AAG GCT TAA TCA AAA 981        990         999        1008        1017        1026
         GAC TGG AAA ACT GCA GTC TGT AAT AGC ATA AGG CTT CCA TTA TGA AAG AAA ACT 1035       1044        1053        1062        1071        1080
         ACA AAA ATA ATA CTT CTT TTC CAC CCG TCT TTG GTA TGT ATT GGC TAA TAA AAT 1089       1098        1107        1116
         CAG TTC TGT GGA ACT GGG AAA AAA AAA AAA AAA AAA AAA AAA A 3'
```

FIGURE 1C

```
 1   M A S S F - - L P A G A I T G D S G G E   DBIH
 1   M W G D L W L L P P A S A N P G T G T E   GI 181478
 1   - - - - - - - - - - - - - - - - - - S Q   GI 118276
 1   - - - - - - - - - - - - - - - - - - S Q   GI 118275

19   L S S G D D S G E V E F P H S P E I E E   DBIH
21   A E - - - - - - - - - - - - - - - - - -   GI 181478
 3   A E - - - - - - - - - - - - - - - - - -   GI 118276
 3   A E - - - - - - - - - - - - - - - - - -   GI 118275

39   T S C L A E L F E K A A A H L Q G L I Q   DBIH
23   - - - - - - - F E K A A E E V R H L K T   GI 181478
 5   - - - - - - - F E K A A E E V R H L K T   GI 118276
 5   - - - - - - - F D K A A E E V K H L K T   GI 118275

59   V A S R E Q L L Y L Y A R Y K Q V K V G   DBIH
36   K P S D E E M L F I Y G H Y K Q A T V G   GI 181478
18   K P S D E E M L F I Y G H Y K Q A T V G   GI 118276
18   K P A D E E M L F I Y S H Y K Q A T V G   GI 118275

79   N C N T P K P S F F D F E G K Q K W E A   DBIH
56   D I N T E R P G M L D F T G K A K W D A   GI 181478
38   D I N T E R P G M L D F T G K A K W D A   GI 118276
38   D I N T E R P G M L D F K G K A K W D A   GI 118275

99   W K A L G D S S P S Q A M Q E Y I A V V   DBIH
76   W N E L K G T S K E D A M K A Y I N K V   GI 181478
58   W N E L K G T S K E D A M K A Y I N K V   GI 118276
58   W N E L K G T S K E D A M K A Y I D K V   GI 118275
```

FIGURE 2A

```
119  K K L D P G W N P Q I P E K K R K R S K   DBIH
 96  E E L - - - - - - - - - - - - - - K K K   GI 181478
 78  E E L - - - - - - - - - - - - - - K K K   GI 118276
 78  E E L - - - - - - - - - - - - - - K K K   GI 118275

139  Y K V W A S Y                              DBIH
102  Y G I                                      GI 181478
 84  Y G I                                      GI 118276
 84  Y G I                                      GI 118275
```

FIGURE 2B

```
              10         20         30         40         50         60         70
        MASSFLPAGAITGDSGGELSSGDDSGEVEFPHSPEIEETSCLAELFEKAAAHLQGLIQVASREQLLYLYA
HELIX   HHHHHh                                  hhhhHHHHHHHHHhhhhhhhhhh
SHEET                                                     sssssss        SSSSSSSSSSSSSSS
TURN            TTTTT TTTTTTTTTTTTT  TTTTTT TTTT
COIL                   C             CC     C 80         90        100        110        120        130        140
        RYKQVKVGNCNTPKPSFFDFEEGKQKWEAWKALGDSSPSQAMQEYIAVVKKLDPGWNPQIPEKKRKRSKYK
HELIX   hhhhhhh             hhHHHHHHHHHHHh           hHHHHHHHHHHH          HHhh     h
SHEET   SSSSSSs        sSSs                      sssSSSSSSSSSS     sssss                s
TURN         TTTTTTTTTT                TTTTTTTTT             TTTTTTT         TTTTTTT
COIL                                                                     CC VWASY
HELIX   hhH
SHEET   SSsSS
TURN
COIL
```

FIGURE 4

HUMAN DBI/ACBP-LIKE PROTEIN

FIELD OF THE INVENTION

The present invention relates to nucleic acid and amino acid sequences of a novel human DBI/ACBP-like protein and to the use of these sequences in the diagnosis, study, prevention and treatment of disease.

BACKGROUND OF THE INVENTION

Diazepam binding inhibitor/acyl-CoA binding protein (DBI/ACBP)-like protein is a 10 kdal protein found in species ranging from yeast to mammals. It is expressed in a variety of organs and tissues. Originally, DBI was purified from rat brain based on its ability to displace diazepam from type A gamma-aminobutyrate ($GABA_A$) receptors (Guidotti et al (1983) Proc Nat Acad Sci U.S.A. 80:3531–3535). An acyl-Coenzyme A (acyl-CoA) binding protein (ACBP) subsequently purified from liver was found to be identical to DBI (Mikkelsen J. et al (1987) Biochem J 245:857–861). The protein was known as endozepine, DBI, or ACBP, but it is now generally referred to as DBI/ACBP. DBI/ACBP, and polypeptides derived from it, have been implicated in multiple biological processes, such as 1) $GABA_A$/benzodiazepam receptor modulation, 2) acyl-CoA metabolism, 3) steroidogenesis, and 4)insulin secretion (reviewed in Knudsen J. et al (1993) Mol Cell Biochem 123:129–138).

The three-dimensional solution structure of bovine DBI/ACBP with and without bound acyl-CoA ligands has been solved by NMR (Andersen K. V. and Poulsen F. M. (1992) J Mol Biol 226:1131–41; Kragelund et al (1993) J Mol Biol 230:1260–1277). DBI/ACBP consists of four alpha helices (A1 through A4) arranged in a left-handed anti-parallel bundle, with parallel helices A1 and A4 anti-parallel to helices A2 and A3. Helix A2 interacts with each of the other three helices in a structure reminiscent of a bowl. The inner surface of the bowl has a patch of non-polar and uncharged residues at the interface between helices A2 and A3. The rims of the bowl have mainly polar and charged groups which are contributed by the hydrophilic residues of the amphipathic helices. The ligand binding site is located on the inner surface of the bowl, and it binds the aliphatic acyl chain of the fatty acyl-CoA ligand in a non-polar arrangement created partly by the protein and partly by the pantetheine and the adenosine-3'-phosphate of CoA. The pantetheine and CoA moieties likewise form a highly polar and charged surface, so that the surface together with the polar and charged rims of the protein bowl ensure the solubility of the entire complex (Kragelund et al, supra).

The binding affinity of bovine DBI/ACBP towards acyl-CoA esters depends on the length of the acyl chain, where the highest affinity is for long-chain (C14 to C22) acyl-CoA esters. The protein is very specific in binding acyl-CoA esters, binding neither free CoA nor free fatty acids (Rosendal J. et al (1993) Biochem J 290:321–326). DBI/ACBP sequesters bound long-chain fatty acyl-CoA, protects acyl-CoAs from hydrolysis, extracts acyl-CoAs from phosphatidyl choline membranes, and mediates intermembrane acyl-CoA transport (Rasmussen et al (1994) Biochem J 299:165–170). The overexpression of DBI/ACBP in rapidly growing brain tumors such as astrocytomas, glioblastomas and medullablastomas suggests that it may be involved in the regulation of high-energy acyl-CoA metabolism in rapidly growing neuronal cells (Alha H. et al (1995) Cell Growth Differ 6:309–314).

DBI/ACBP also inhibits the binding of benzodiazepines to the $GABA_A$ receptor. The $GABA_A$ receptor is a postsynaptic $Cl^-$ channel. The $Cl^-$ ion channel opening burst, elicited by the inhibitory neurotransmitter GABA, is prolonged by benzodiazepines. Benzodiazepines thereby enhance GABA-mediated synaptic inhibitory responses and reduce pathological anxiety. DBI/ACBP or its proteolytic fragments, most notably octadecaneneuropeptide (ODN, DBI/ACBP amino acids 32–50), suppress the anxiety-reducing effect of the benzodiazepines. Expression of DBI/ACBP is increased in brain and cerebrospinal fluid of patients diagnosed with neurological disorders such as hepatic encephalopathy, depression and anxiety (Costa E. and Guidotti A. (1991) Life Sciences 49:325–344).

DBI/ACBP is also involved in the regulation of steroid biosynthesis in mitochondria (Garnier et al (1993) Endocrinology 132:444–458). DBI/ACBP stimulates mitochondrial steroidogenesis in the adrenal gland by facilitating cholesterol delivery to the inner mitochondrial membrane (Yanagibashi K. (1988) Endocrinology 123:2075–2082). Knudsen et al (1993, supra) suggest that DBI/ACBP may also scavenge fatty acyl-CoA esters produced from fatty acids released in the conversion of cholesterol to steroids. Antisense oligonucleotides to DBI/ACBP inhibit hormone-stimulated steroid production in Leydig cells of rat testis (Boujrad N. et al (1993) Proc Nat Acad Sci U.S.A 90:5728–5731).

DBI/ACBP has been found in all tissues tested; the highest amounts have been found in liver, kidney, brain, adrenal gland, intestine and salivary gland (Knudsen J. et al, supra,. Immunohistochemical localization indicates DBI/ACBP is selectively expressed in specialized cells within a given organ. Elevated levels of DBI/ACBP have been found in cells of the adrenal cortex and testis which produce steriods, and in liver hepatocytes which are involved in steriod and fat metabolism. Elevated levels of DBI/ACBP have also been found in epithelial cells of kidney tubules, the upper intestinal tracts and large bronchioles, cells which are specialized for water and electrolyte absorption and secretion. In brain high DBI/ACBP concentrations are found in choroid plexus and circumventricular organs, which are specialized for the control of secretion and osmolality of cerebrospinal fluid (Bovolin et al (1990) Reg Peptides 29:267–281).

The selective modulation of the expression or activity of a novel tissue-specific DBI/ACBP-like protein may allow the successful management of diseases or biochemical abnormalities relating to the tissues in which it is expressed. In addition, the binding properties of this small protein may be utilized in drug delivery applications as a soluble carrier for otherwise insoluble therapeutic molecules.

SUMMARY OF THE INVENTION

The present invention discloses a novel tissue-specific DBI/ACBP-like protein, hereinafter referred to as DBIH, having chemical and structural homology to isoforms of human DBI/ACBP and bovine DBI/ACBP. Accordingly, the invention features a substantially purified DBI/ACBP-like protein, encoded by amino acid sequence of SEQ ID NO:1, having structural characteristics of the family of DBI/ACBPs including those from human and cow.

One aspect of the invention features isolated and substantially purified polynucleotides which encode DBIH. In a particular aspect, the polynucleotide is the nucleotide sequence of SEQ ID NO:2. In addition, the invention features nucleotide sequences which hybridize under stringent conditions to SEQ ID NO:2.

The invention further relates to nucleic acid sequence encoding DBIH, oligonucleotides, peptide nucleic acids (PNA), fragments, portions or antisense molecules thereof. The present invention also relates to an expression vector which includes polynucleotide encoding DBIH and its use to transform host cells or organisms. The invention also relates to antibodies which bind specifically to the DBI of SEQ ID NO:1 and to a pharmaceutical composition comprising a substantially purified DBI of SEQ ID NO:1.

BRIEF DESCRIPTION OF THE FIGURES

FIGS. 1A, 1B and 1C show the amino acid sequence (SEQ ID NO:1) and the nucleic acid sequence (SEQ ID NO:2) of the human DBI/ACBP-like protein DBIH, produced using MacDNAsis software (Hitachi Software Engineering Co Ltd, San Bruno Calif.).

FIG. 2A and 2B show the amino acid sequence alignments among DBIH (SEQ ID NO:1), the 104 amino acid human DBI/ACBP isoform (GI 181478; SEQ ID NO:3), the 86 amino acid human DBI/ACBP isoform (GI 118276; SEQ ID NO:4), and the 86 amino acid bovine DBI/ACBP (GI 118275, SEQ ID NO:5), produced using the multisequence alignment program of DNAStar software (DNAStar Inc, Madison Wis.).

FIG. 4 shows the predicted secondary structure (generated using MacDNAsis software) of DBIH, SEQ ID NO:1.

DETAILED DESCRIPTION OF THE INVENTION

Definitions

Figure 3:
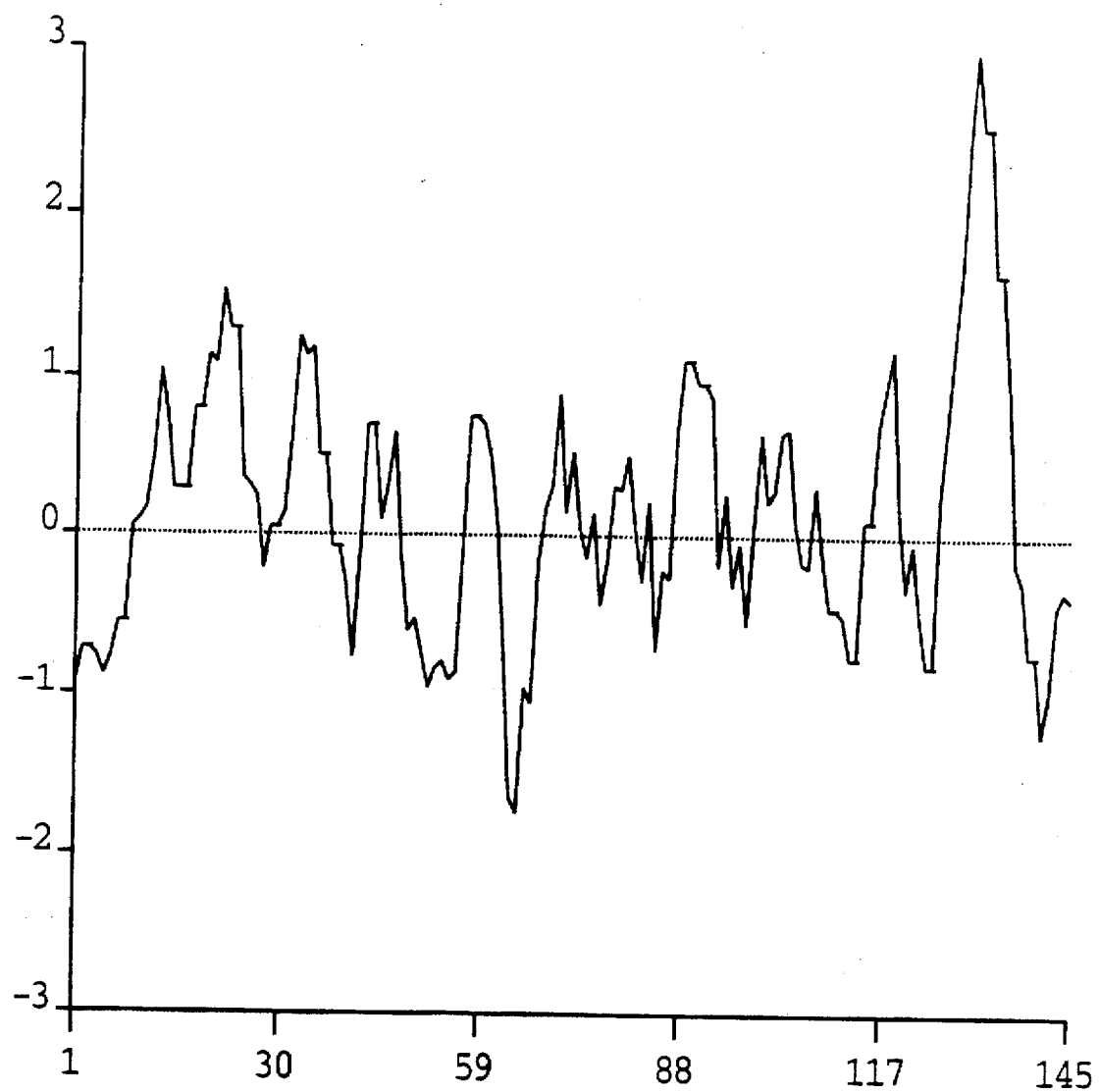
FIG. 3 shows the hydrophobicity plot (generated using MacDNAsis software) for DBIH, SEQ ID NO:1; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P. E. et al (1993) Anticancer Drug Des 8:53–63).

A "variant" of DBIH is defined as an amino acid sequence that is different by one or more amino acid substitutions. The variant may have "conservative" changes, wherein a substituted amino acid has similar structural or chemical properties, eg. replacement of leucine with isoleucine. More rarely, a variant may have "nonconservative" changes, e.g., replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring DBIH.

A "substitution" results from the replacement of one or more nucleotides or amino acids by different nucleotides or amino acids, respectively.

The term "biologically active" refers to a DBIH having structural, regulatory or biochemical functions of the naturally occurring DBIH. Likewise, "immunologically active" defines the capability of the natural, recombinant or synthetic DBIH, or any oligopeptide thereof, to induce a specific immune response in appropriate animals or cells and to bind with specific antibodies.

The term "derivative" as used herein refers to the chemical modification of a nucleic acid encoding DBIH or the encoded DBIH. Illustrative of such modifications would be replacement of hydrogen by an alkyl, acyl, or amino group. A nucleic acid derivative would encode a polypeptide which retains essential biological characteristics of natural DBIH.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J. (1994) *Dictionary of Biotechnology*, Stockton Press, New York N.Y.). Amplification as carried out in the polymerase chain reaction technologies is described in Dieffenbach C. W. and G. S. Dveksler (1995, *PCR Primer, a Laboratory Manual*, Cold Spring Harbor Press, Plainview N.Y.).

Description

The present invention relates to a novel human DBI/ACBP-like protein, designated DBIH, initially identified among the partial cDNAs from a human paraganglia tissue library (PGANNOT01) and to the use of the nucleic acid and amino acid sequences disclosed herein in the study, diagnosis, prevention and treatment of disease. Northern analysis using the LIFESEQ™ database (Incyte Pharmaceuticals, Palo Alto Calif.) indicates that DBIH-encoding mRNA is only present in paraganglia, in contrast to the wide tissue distribution of the DBI/ACBPs. Paraganglia contain cells that synthesize, store and secrete catecholamines. Cells of the paraganglia receive sympathetic preganglionic innervation similar to that of chromaffin cells of the adrenal medulla. The paraganglia are well vascularized and the secretory cells are generally located next to capillaries. With little obstruction to the passage of hormones, paraganglial cells have both remote and local endocrine effects.

The present invention also encompasses DBIH variants. A preferred DBIH variant is one having at least 80% amino acid sequence similarity to the DBIH amino acid sequence (SEQ ID NO:1), a more preferred DBIH variant is one having at least 90% amino acid sequence similarity to SEQ ID NO:1 and a most preferred DBIH variant is one having at least 95% amino acid sequence similarity to SEQ ID NO:1.

The nucleic acid sequence encoding a portion of DBIH was first identified in the cDNA, Incyte Clone 620984, through a computer-generated search for amino acid sequence alignments. The nucleic acid sequence, SEQ ID NO:2, disclosed herein (FIGS. 1A, 1B and 1C) (encodes the amino encodes the amino acid sequence, SEQ ID NO:1, designated DBIH. The present invention is based in part on the structural homology shown in FIGS. 2A and 2B, among DBIH and other DBI/ACBPs including two human isoforms (GI 181478; Gray P. W. et al (1986) Proc Nat Acad Sci U.S.A 83:7547–7551 and GI 118276; Marquardt H. et al (1986) J Biol Chem 261:9727–9731), and one bovine isoform (GI 118275, Marquardt H. et al, supra). GI 181478, GI 118276, and GI 118275 have, respectively, 39%, 42% and 40% sequence identity with DIBH.

DBIH consists of 145 amino acids and, based on the hydropathy plot (FIG. 3) and the secondary structure prediction (FIG. 4), is a soluble protein consisting of at least four helical segments. These helices may form an antiparallel bowl-shaped array which defines the class of small ligand-binding proteins including the DBI/ACBPs (Kregelund et al, supra). From its homology to the central portion of human and bovine DBI/ACBPs, the four alpha-helices of DBIH are predicted to include residues at or near positions 45–56, 61–77,92–103, and 106-121. In comparison with the 86 residue human and bovine DBI/ACBPs (GI 118276 and GI 118275, respectively), DBIH contains an additional 40 amino acids at the N-terminus and an additional 14 amino acids near the C-terminus (FIGS. 2A and 2B). The 104 amino acid human DBI/ACBP isoform (GI 181478) likewise contains an additional 23 amino acids near the N-terminus compared to the 86 residue forms. The additional residues in DBIH at the N- and C-termini do not have significant alpha-helical content (FIG. 4), and contain a large proportion of hydrophilic charged residues, indicating they are not likely to be membrane-spanning or signal sequences. However, the additional residues at the N- or C-termini of DBIH may be proteolytically processed to yield smaller forms of DBIH in vivo.

THE DBIH CODING SEQUENCES

The nucleic acid and amino acid sequences of DBIH are shown in FIGS. 1A, 1B and 1C. In accordance with the invention, any nucleic acid sequence which encodes the amino acid sequence of DBIH can be used to generate recombinant molecules which express DBIH. In a specific embodiment described herein, a partial sequence of DBIH was first isolated as Incyte Clone 620984 from a human paraganglia tissue library (PGANNOT01).

It will be appreciated by those skilled in the art that as a result of the degeneracy of the genetic code, a multitude of DBIH-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring DBIH, and all such variations are to be considered as being specifically disclosed.

Although nucleotide sequences which encode DBIH and its variants are preferably capable of hybridizing to the nucleotide sequence of the naturally occurring DBIH under appropriately selected conditions of stringency, it may be advantageous to produce nucleotide sequences encoding DBIH or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding DBIH and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a DBIH and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a gene encoding DBIH.

Also included within the scope of the present invention are polynucleotide sequences that are capable of hybridizing to the nucleotide sequence of FIGS. 1A, 1B and 1C under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and confer may be used at a defined stringency.

Altered nucleic acid sequences encoding DBIH which may be used in accordance with the invention include deletions, insertions or substitutions of different nucleotides resulting in a polynucleotide that encodes the same or a functionally equivalent DBIH. The protein may also show deletions, insertions or substitutions of amino acid residues which produce a silent change and result in a functionally equivalent DBIH. Deliberate amino acid substitutions may be made on the basis of similarity in polarity, charge, solubility, hydrophobicity, hydrophilicity, and/or the amphipathic nature of the residues as long as the biological activity of DBIH is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of DBIH. As used herein, an "allele" or "allelic sequence" is an alternative form of DBIH. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (U.S. Biochemical Corp, Cleveland Ohio), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

EXTENDING THE POLYNUCLEOTIDE SEQUENCE

The polynucleotide sequence encoding DBIH may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J. D. et al (1991; Nucleic Acids Res 19:3055–60). Additionally, one can use PCR, nested primers and PromoterFinder libraries to walk in genomic DNA (PromoterFinder™ Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851–8).

EXPRESSION OF THE NUCLEOTIDE SEQUENCE

In accordance with the present invention, polynucleotide sequences which encode DBIH, fragments of the polypeptide, fusion proteins or functional equivalents thereof may be used in recombinant DNA molecules that direct the expression of DBIH in appropriate host cells. Due to the inherent degeneracy of the genetic code, other DNA sequences which encode substantially the same or a functionally equivalent amino acid sequence, may be used to clone and express DBIH. As will be understood by those of skill in the art, it may be advantageous to produce DBIH-encoding nucleotide sequences possessing non-naturally occurring codons. Codons preferred by a particular prokaryotic or eukaryotic host (Murray E. et al (1989) Nuc Acids Res 17:477–508) can be selected, for example, to increase the rate of DBIH expression or to produce recombinant RNA transcripts having desirable properties, such as a longer half-life, than transcripts produced from naturally occurring sequence.

The nucleotide sequences of the present invention can be engineered in order to alter a coding sequence of DBIH for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant nucleotide sequence encoding DBIH may be ligated to a heterologous sequence to encode a fusion protein. For example, for screening of peptide libraries for inhibitors of DBIH activity, it may be useful to encode a chimeric DBIH protein that is recognized by a commercially available antibody. A fusion protein may also be engineered to contain a cleavage site located between a DBIH sequence and the heterologous protein sequence, so that the DBIH may be cleaved and substantially purified away from the heterologous moiety.

In an alternate embodiment of the invention, the coding sequence for DBIH may be synthesized, whole or in part, using chemical methods well known in the art (see Caruthers M. H. et al (1980) Nuc Acids Res Symp Ser 215–23, Horn T. et al(1980) Nuc Acids Res Symp Ser 225–32, etc). Alternatively, the protein itself could be produced using chemical methods to synthesize a DBIH amino acid sequence, whole or in part. For example, peptide synthesis can be performed using various solid-phase techniques (Roberge J. Y. et al (1995) Science 269:202–204) and automated synthesis may be achieved, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, W. H. Freeman and Co, New York N.Y.). The composition of the synthetic peptides may be confirmed by amino acid analysis or sequencing (eg, the Edman degradation procedure; Creighton, supra). Additionally the amino acid sequence of DBIH, or any part thereof, may be altered during direct synthesis and/or combined using chemical methods with sequences from other proteins, or any part thereof, to produce a variant polypeptide.

EXPRESSION SYSTEMS

In order to express a biologically active DBIH, the nucleotide sequence encoding DBIH or its functional equivalent, is inserted into an appropriate expression vector, ie, a vector which contains the necessary elements for the transcription and translation of the inserted coding sequence.

Methods which are well known to those skilled in the art can be used to construct expression vectors containing a DBIH coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F. M. et al (1989) *Current Protocols in Molecular Biology*, John Wiley & Sons, New York N.Y.

A variety of expression vector/host systems may be utilized to contain and express a DBIH coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif. or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of DBIH, vectors based on SV40 or EBV may be used with an appropriate selectable marker.

In bacterial systems, a number of expression vectors may be selected depending upon the use intended for DBIH. For example, when large quantities of DBIH are needed for the induction of antibodies, vectors which direct high level expression of fusion proteins that are readily purified may be desirable. Such vectors include, but are not limited to, the multifunctional *E. coil* cloning and expression vectors such as Bluescript® (Stratagene), in which the DBIH coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding DBIH may be driven by any of a number of promoters. For example, vital promoters such as the 35S and 19S promoters of CaMV (Brisson et al (1984) Nature 310:511–514) may be used alone or in combination with the omega leader sequence from TMV (Takamatsu et al (1987) EMBO J 6:307–311. Alternatively, plant promoters such as the small subunit of RUBISCO (Coruzzi et al (1984) EMBO J 3:1671–1680; Broglie et al (1984) Science 224:838–843); or heat shock promoters (Winter J. and Sinibaldi R. M. (1991) Results Probl Cell Differ 17:85–105) may be used. These constructs can be introduced into plant cells by direct DNA transformation or pathogen-mediated transfection. For reviews of such techniques, see Hobbs S. or Murry L. E. in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express DBIH is an insect system. In one such system, *Autographa californica* nuclear polyhedrosis virus (AcNPV) is used as a vector to express foreign genes in *Spogdoptera frugiperda* cells or in Trichoplusia larvae. The DBIH coding sequence may be cloned into a nonessential region of the virus, such as the polyhedrin gene, and placed under control of the polyhedrin promoter. Successful insertion of the DBIH coding sequence will render the polyhedrin gene inactive and produce recombinant virus lacking coat protein coat. The recombinant viruses are then used to infect *S. frugiperda* cells or Trichoplusia larvae in which DBIH is expressed (Smith et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, a coding sequence for DBIH may be ligated into an adenovirus transcription/translation complex consisting of the late promoter and tripartite leader sequence. Insertion in a nonessential E1 or E3 region of the viral genome will result in a viable virus capable of expressing DBIH in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a DBIH sequence. These signals include the ATG initiation codon and adjacent sequences. In cases where nucleic acid encoding DBIH, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D. et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express DBIH may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M. et al (1977) Cell 11:223–32) and adenine phosphoribosyltransferase (Lowy I. et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M. et al (1980) Proc Natl Acad Sci 77:3567–70); npt, which confers resistance to the aminoglycosides neomycin and G-418 (Colbere-Garapin F. et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C. A. et al (1995) Methods Mol Biol 55:121–131).

IDENTIFICATION OF TRANSFORMANTS CONTAINING THE POLYNUCLEOTIDE SEQUENCE

Although the presence/absence of marker gene expression suggests that the gene of interest is also present, its presence and expression should be confirmed. For example, if the DBIH polynucleotide sequence is inserted within a marker gene sequence, recombinant cells containing DBIH can be identified by the absence of marker gene function. Alternatively, a marker gene can be placed in tandem with a DBIH sequence under the control of a single promoter. Expression of the marker gene in response to induction or selection usually indicates expression of the tandem DBIH as well.

Alternatively, host cells which contain the coding sequence for DBIH and express DBIH may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding DBIH can be detected by DNA-DNA or DNA-RNA hybridization or amplification using probes, portions or fragments of DBIH-encoding nucleotides. Nucleic acid amplification based assays involve the use of oligonucleotides or oligomers based on the DBIH sequence to detect transformants containing DBIH DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of DBIH, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on DBIH is preferred, but a competitive binding assay may be employed. These and other assays are described, among other places, in Hampton R. et al (1990, Serological Methods, a Laboratory Manual, APS Press, St Paul Minn.) and Maddox D. E. et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to DBIH include oligolabeling, nick translation, end-labeling or PCR amplification using a labeled nucleotide. Alternatively, the DBIH sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and U.S. Biochemical Corp (Cleveland Ohio supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

PURIFICATION OF DBIH

Host cells transformed with a DBIH-encoding nucleotide sequence may be cultured under conditions suitable for the expression and recovery of the encoded protein from cell culture. The protein produced by a recombinant cell may be contained intracellularly or secreted depending on the sequence and/or the vector used. As will be understood by those of skill in the art, expression vectors containing DBIH can be designed for efficient production and proper transmembrane insertion of DBIH into a prokaryotic or eukaryotic cell membrane. Other recombinant constructions may join DBIH to nucleotide sequence encoding a polypeptide domain which will facilitate purification of soluble proteins (Kroll D. J. et al (1993) DNA Cell Biol 12:441–53; cf discussion of vectors infra containing fusion proteins).

DBIH may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and DBIH is useful to facilitate purification. One such expression vector provides for expression of a fusion protein compromising an DBIH and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3:263–281) while the enterokinase cleavage site provides a means for purifiying the DBI from the fusion protein.

In addition to recombinant production, fragments of DBIH may be produced by direct peptide synthesis using solid-phase techniques (cf Stewart et al (1969) *Solid-Phase Peptide Synthesis*, W. H. Freeman Co, San Francisco; Merrifield J. (1963) J Am Chem Soc 85:2149–2154). In vitro protein synthesis may be performed using manual techniques or by automation. Automated synthesis may be achieved, for example, using Applied iosystems 431A Peptide Synthesizer (Perkin Elmer, Foster City Calif.) in accordance with the instructions provided by the manufacturer. Various fragments of DBIH may be chemically synthesized separately and combined using chemical methods to produce the full length molecule.

USES OF DBIH

The rationale for the use of polynucleotide and polypeptide sequences disclosed herein is based in part on the chemical and structural homology among the novel DBIH and the human and bovine isoforms of DBI/ACBP. DBIH may be used in the diagnosis and treatment of conditions, disorders or diseases associated with abnormal function of paraganglia, including paragangliomas.

The clinical features and morbidity of paragangliomas are due predominantly to the abnormal release of catecholamines. Hypertension is the most common manifestation. Paraganglioma is a correctable cause of high blood pressure. Indeed, it is rarely fatal if properly diagnosed and treated.

DBIH may be useful in the regulation of the biosynthesis or metabolism of biological molecules such as catecholamines in paraganglia. Molecules associated with paraganglial function, or their precursors or metabolic products, may bind to DBIH in a manner analogous to that of fatty acyl-CoAs to DBI/ACBP. DBIH may sequester and protect the bound ligand from unwanted side-reactions such as hydrolysis or oxidation, or present the bound ligand to a receptor molecule. Alternatively, DBIH or a fragment thereof may act as a neuromodulator of catecholamine-induced responses in paraganglia.

DBIH or its fragments can be used to identify specific molecules which it sequesters or with which it interacts. In this regard, DBIH may also be used to sequester therapeutic agents, specifically binding the drug so that the complex is water-soluble and suitable for therapeutic delivery.

In overexpression of DBIH associated with paraganglia-related disorders, it may be advantageous to suppress DBIH. DBIH could be suppressed by administration of antisense oligonucleotides. Alternatively, antibodies specifically recognizing the active site of DBIH may be introduced to treat diseases or conditions associated with abnormal DBIH activity.

The structure of DBIH also allows its use in delivery of other therapeutic molecules. DBIH may bind therapeutic agents or drugs which are ordinarily insoluble or only slightly soluble in water. The high charge density of the DBIH molecule renders the protein-ligand complex soluble in an aqueous environment. The specificity and binding affinities of DBIH for therapeutic ligands may be manipulated by protein engineering techniques known to those skilled in the art.

DBIH ANTIBODIES

DBIH-specific antibodies are useful for the diagnosis of conditions and diseases associated with expression of DBIH. Such antibodies may include, but are not limited to, polyclonal, monoclonal, chimeric, single chain, Fab fragments and fragments produced by a Fab expression library. Neutralizing antibodies, i.e., those which inhibit dimer formation, are especially preferred for diagnostics and therapeutics.

DBIH for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of DBIH amino acids may be fused with those of another protein such as keyhole limpet hemocyanin and antibody produced against the chimeric molecule. Procedures well known in the art can be used for the production of antibodies to DBIH.

For the production of antibodies, various hosts including goats, rabbits, rats, mice, etc may be immunized by injection with DBIH or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*bacilli*Calmette-Guerin) and *Corynebacterium parvum* are potentially useful human adjuvants.

Monoclonal antibodies to DBIH may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R. Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S.

Pat. No. 4,946,778) can be adapted to produce DBIH-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G. and Milstein C. (1991; Nature 349:293–299).

Antibody fragments which contain specific binding sites for DBIH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W. D. et al (1989) Science 256:127–1281).

A variety of protocols for competitive binding or immunoradiometric assays using either polyclonal or monoclonal antibodies with established specificities are well known in the art. Such immunoassays typically involve the formation of complexes between DBIH and its specific antibody and the measurement of complex formation. A two-site, monoclonal-based immunoassay utilizing monoclonal antibodies reactive to two noninterfering epitopes on a specific DBIH protein is preferred, but a competitive binding assay may also be employed. These assays are described in Maddox D. E. et al (1983, J Exp Med 158:1211).

DIAGNOSTIC ASSAYS USING DBIH SPECIFIC ANTIBODIES

Particular DBIH antibodies are useful for the diagnosis of conditions or diseases characterized by expression of DBIH or in assays to monitor patients being treated with DBIH, agonists or inhibitors. Diagnostic assays for DBIH include methods utilizing the antibody and a label to detect DBIH in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring DBIH, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on DBIH is preferred, but a competitive binding assay may be employed. These assays are described, among other places, in Maddox, D. E. et al (1983, J Exp Med 158:1211).

In order to provide a basis for diagnosis, normal or standard values for DBIH expression must be established. This is accomplished by combining body fluids or cell extracts taken from normal subjects, either animal or human, with antibody to DBIH under conditions suitable for complex formation which are well known in the art. The amount of standard complex formation may be quantified by comparing various artificial membranes containing known quantities of DBIH with both control and disease samples from biopsied tissues. Then, standard values obtained from normal samples may be compared with values obtained from samples from subjects potentially affected by disease. Deviation between standard and subject values establishes the presence of disease state.

DRUG SCREENING

DBIH, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between DBIH and the agent being tested, may be measured.

Another technique for drug screening which may be used for high throughput screening of compounds having suitable binding affinity to the DBIH is described in detail in "Determination of Amino Acid Sequence Antigenicity" by Geysen H. N., WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of DBIH and washed. Bound DBIH is then detected by methods well known in the art. Substantially purified DBIH can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding DBIH specifically compete with a test compound for binding DBIH. In this manner, the antibodies can be used to detect the presence of any peptide which shares one or more antigenic determinants with DBIH.

USES OF THE POLYNUCLEOTIDE ENCODING DBIH

A polynucleotide encoding DBIH, or any part thereof, may be used for diagnostic and/or therapeutic purposes. For diagnostic purposes, the DBIH of this invention may be used to detect and quantitate gene expression in biopsied tissues in which expression of DBIH may be implicated. The diagnostic assay is useful to distinguish between absence, presence, and excess expression of DBIH and to monitor regulation of DBIH levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding DBIH or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring DBIH, alleles or related sequences.

Probes may also be used for the detection of related sequences and should preferably contain at least 50% of the nucleotides from any of these DBIH encoding sequences. The hybridization probes of the subject invention may be derived from the nucleotide sequence of SEQ ID NO:2 or from genomic sequence including promoter, enhancer elements and introns of the naturally occurring DBIH. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

Other means for producing specific hybridization probes for DBIH DNAs include the cloning of nucleic acid sequences encoding DBIH or DBIH derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostics

Polynucleotide sequences encoding DBIH may be used for the diagnosis of conditions or diseases with which the expression of DBIH is associated. For example, polynucleotide sequences encoding DBIH may be used in hybridization or PCR assays of fluids or tissues from biopsies to detect DBIH expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The DBIH nucleotide sequence disclosed herein provide the basis for assays that detect activation or induction associated with inflammation or disease. The DBIH nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of DBIH nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for DBIH expression must be established. This is accomplished by combining body fluids or cell extracts taken from normal subjects, either animal or human, with DBIH, or a portion thereof, under conditions suitable for hybridization or amplification. Standard hybridization may be quantified by comparing the values obtained for normal subjects with a dilution series of DBIH run in the same experiment where a known amount of substantially purified DBIH is used. Standard values obtained from normal samples may be compared with values obtained from samples from patients afflicted with DBIH-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polymerase Chain Reaction (PCR) as described in U.S. Pat. Nos. 4,683,195 and 4,965,188 provides additional uses for oligonucleotides based upon the DBIH sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P. C. et al 1993 J Immunol Methods 159:235–44) or biotinylating (Duplaa C. et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to the genes encoding the DBI/ACBPs and its expression profile, the DBIH polynucleotide disclosed herein may provide the basis for the design of molecules for the treatment of diseases associated with abnormal function in paraganglia.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense DBIH. See, for example, the techniques described in Sambrook et al (supra) and Ausubel et al (supra).

The polynucleotides comprising full length cDNA sequence and/or its regulatory elements enable researchers to use DBIH as an investigative tool in sense (Youssoufian H. and H. F. Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding DBIH can be turned off by transfecting a cell or tissue with expression vectors which express high levels of a desired DBIH fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

A mentioned above, modifications of gene expression can be obtained by designing antisense molecules, DNA, RNA or PNA, to the control regions of DBIH, i.e., the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes.

Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al (In: Huber B. E. and B. I. Carr (1994) *Molecular and Immunologic Approaches*, Futura Publishing Co. Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of RNA encoding DBIH.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding DBIH. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for DBIH disclosed herein may be used in molecular biology techniques that have not yet been developed, provided the new techniques rely on properties of nucleotide sequences that are currently known, including but not limited to such properties as the triplet genetic code and specific base pair interactions.

DETECTION AND MAPPING OF RELATED POLYNUCLEOTIDE SEQUENCES

The nucleic acid sequence for DBIH can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a DBIH on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, an STS based map of the human genome was recently published by the Whitehead-NIT Center for Genomic Research (Hudson T. J. et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

PHARMACEUTICAL COMPOSITIONS

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of DBIH, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

The examples below are provided to illustrate the subject invention and are not included for the purpose of limiting the invention.

EXAMPLES

I cDNA Library Construction

The normal tissue used for paraganglion cDNA library construction was obtained from a 46 year-old male (Lot #0084; Mayo Clinic, Rochester Minn). The frozen tissue was homogenized and lysed in guanidinium isothiocyanate solution using a Brinkmann Homogenizer Polytron PT-3000 (Brinkmann Instruments, Westbury N.J.). The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted twice with acid phenol pH 4.0 following Stratagene's RNA isolation protocol and precipitated using 0.3M sodium acetate and 2.5 volumes of ethanol, resuspended in DEPC-treated water and DNase treated for 15 min at 37° C. The reaction was stopped with an equal volume of acid phenol and the RNA was isolated using the Qiagen Oligotex kit (QIAGEN Inc, Chatsworth Calif.) and used to construct the cDNA library.

The RNA was handled according to the recommended protocols in the SuperScript Plasmid System for cDNA Synthesis and Plasmid Cloning (catalog #18248-013; Gibco/BRL), and cDNAs were ligated into pSport I. The plasmid pSport I was subsequently transformed into DH5a™ competent cells (Cat. #18258-012, Gibco/BRL).

II Isolation and Sequencing of cDNA Clones

Plasmid DNA was released from the cells and purified using the Miniprep Kit (Catalogue #77468; Advanced Genetic Technologies Corporation, Gaithersburg Md. This kit consists of a 96 well block with reagents for 960 purifications. The recommended protocol was employed except for the following changes: 1) the 96 wells were each filled with only 1 ml of sterile Terrific Broth (Catalog #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS™ DNA Purification System (Catalogue #A7100, Promega, Madison Wis.)or QIAwell™-8 Plasmid, QIAwell PLUS DNA and QIAwell ULTRA DNA Purification Systems (QIAGEN® Chatsworth Calif.).

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from M. J. Research, Watertown Mass.) and Applied Biosystems 377 or 373 DNA Sequencing Systems (Perkin Elmer), and the reading frame was determined.

III Homology Searching of cDNA Clones and Their Deduced Proteins

Each cDNA was compared to sequences in GenBank using a search algorithm developed by Applied Biosystems and incorporated into the INHERIT-670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques use BLAST (Altschul S. F. 1993 and 1990, supra) to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of DBIH to Full Length or to Recover Regulatory Elements

The nucleic acid sequence encoding full length DBIH (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known DBIH nucleotide sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Frimer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook J. et al, supra). After incubation for one hour at 37° C., the whole transformation mixture is plated on Luria Bertani (LB)-agar (Sambrook J. et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [γ-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The nucleotide sequence encoding DBIH, or any part thereof, is used to inhibit in vivo or in vitro expression of naturally occurring DBIH. Although use of antisense oligonucleotides, comprising about 20 base-pairs, is specifically described, essentially the same procedure is used with larger cDNA fragments. An oligonucleotide based on the coding sequence of DBIH as shown in FIGS. 1A and 1B is used to inhibit expression of naturally occurring DBIH. The complementary oligonucleotide is designed from the most unique 5' sequence as shown in FIGS. 1A and 1B and used either to inhibit transcription by preventing promoter binding to the upstream nontranslated sequence or translation of an DBIH transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII Expression of DBIH

Expression of DBIH is accomplished by subcloning the cDNAs into appropriate vectors and transfecting the vectors into host cells. In this case, the cloning vector, pSport, previously used for the generation of the cDNA library is used to express DBIH in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length DBIH. The signal sequence directs the secretion of DBIH into the bacterial growth media which can be used directly in the following assay for activity.

IX DBIH Activity

The binding of a ligand to DBIH is assayed by monitoring the resulting changes in enthalpy (heat production or absorption) in an isothermal titration microcalorimeter (Micro-Cal Inc, Northampton Mass.). Titration microcalorimetry measurements do not require labeling of the ligand or receptor molecules; detection is based solely on the intrinsic change in the heat of enthalpy upon binding. Multiple computer-controlled injections of a known volume of ligand solution are directed into a thermally-controlled chamber containing DBIH. The change in enthalpy after each injection is plotted against the number of injections, producing a binding isotherm. The volumes and concentrations of the injected ligand and of the DBIH solution are used along with the binding isotherm to calculate values for the number, affinity, and association of DBIH with the candidate ligand.

X Production of DBIH Specific Antibodies

DBIH substantially purified using PAGE electrophoresis (Sambrook, supra) is used to immunize rabbits and to produce antibodies using standard protocols. The amino acid sequence translated from DBIH is analyzed using DNAStar software (DNAStar inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIG. 3) is described by Ausubel F. M. et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring DBIH Using Specific Antibodies

Naturally occurring or recombinant DBIH is substantially purified by by immunoaffinity chromatography using antibodies specific for DBIH. An immunoaffinity column is constructed by covalently coupling DBIH antibody to an activated chromatographic resin such as CnBr-activated Sepharose (Pharmacia Biotech). After the coupling, the resin is blocked and washed according to the manufacturer's instructions.

Cellular fractions from cells containing DBIH are prepared by solubilization of the whole cell and isolation of subcellular fractions by differential centrifugation, by the addition of detergent, or by other methods well known in the art. Alternatively, soluble DBIH containing a signal sequence may be secreted in useful quantity into the medium in which the cells are grown.

A fractionated DBIH-containing preparation is passed over the immunoaffinity column, and the column is washed under conditions that allow the preferential absorbance of DBIH (e.g., high ionic strength buffers in the presence of detergent). The column is eluted under conditions that disrupt antibody/DBIH binding (e.g., a buffer of pH 2–3 or a high concentration of a chaotrope such as urea or thiocyanate ion), and DBIH is collected.

XII Identification of Molecules Which Interact with DBIH

DBIH is useful as a research tools for identification, characterization and purification of molecules with which it interacts. In one embodiment of affinity purification, DBIH is covalently coupled to a chromatography column. Cells and their membranes are extracted, endogenous DBIH is removed and various DBIH-free subcomponents are passed over the column. DBIH-associated molecules bind to the column by virtue of their biological affinity. The DBIH-complex is recovered from the column, dissociated and the recovered molecule is subjected to either N-terminal protein sequencing or to high-performance liquid chromatography/mass spectrometry (HPLC/MS). This amino acid sequence or mass spectral analysis is then used to identify the captured molecule or, in the case of a protein ligand, to design degenerate oligonucleotide probes for cloning its gene from an appropriate cDNA library.

In an alternate method, monoclonal antibodies are raised against DBIH and screened to identify those compounds which inhibit the binding of the antibody to DBIH. These monoclonal antibodies are then used in affinity purification or expression cloning of associated molecules.

Other soluble binding molecules are identified in a similar manner. DBIH previously labelled with $^{125}$I Bolton-Hunter reagent (Bolton, A. E. and Hunter, W. M. (1973) Biochem J 133:529) is incubated with extracts or biopsied materials derived from cells or tissues such as paraganglia, rheumatoid synovium, or cerebellum. After incubation, DBIH complexes (which are larger than the size of the purified DBIH molecule) are identified by a sizing technique such as size exclusion chromatography or density gradient centrifugation and are purified by methods known in the art. The soluble binding protein(s) are subjected to N-terminal sequencing or mass spectrometry to obtain information sufficient for database identification, if the soluble protein or molecule is known, or for cloning, if the soluble protein is unknown.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide sequence encoding the polypeptide consisting of SEQ ID NO.1.

2. An isolated and purified polynucleotide sequence consisting of the sequence of SEQ ID NO:2.

3. A polynucleotide sequence consisting of the complement of SEQ ID NO:2.

4. A recombinant expression vector containing a polynucleotide sequence of claim 2.

5. A recombinant host cell consisting of the polynucleotide sequence of claim 2.

6. A method for producing the polypeptide consisting of SEQ ID NO:1, the method comprising the steps of:
   a) culturing the host cell of claim 5 under conditions suitable for the expression of the polypeptide; and
   b) recovering the polypeptide from the host cell culture.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 145 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: PGANNOT01
        ( B ) CLONE: 620984

( x i ) SEQUENCE DESCRIPTION: SEQ ID NO:1:

```
Met Ala Ser Ser Phe Leu Pro Ala Gly Ala Ile Thr Gly Asp Ser Gly
 1               5                  10                  15
Gly Glu Leu Ser Ser Gly Asp Asp Ser Gly Glu Val Glu Phe Pro His
             20                  25                  30
Ser Pro Glu Ile Glu Glu Thr Ser Cys Leu Ala Glu Leu Phe Glu Lys
         35                  40                  45
Ala Ala Ala His Leu Gln Gly Leu Ile Gln Val Ala Ser Arg Glu Gln
     50                  55                  60
Leu Leu Tyr Leu Tyr Ala Arg Tyr Lys Gln Val Lys Val Gly Asn Cys
 65                  70                  75                  80
Asn Thr Pro Lys Pro Ser Phe Phe Asp Phe Glu Gly Lys Gln Lys Trp
                 85                  90                  95
Glu Ala Trp Lys Ala Leu Gly Asp Ser Ser Pro Ser Gln Ala Met Gln
             100                 105                 110
Glu Tyr Ile Ala Val Val Lys Lys Leu Asp Pro Gly Trp Asn Pro Gln
         115                 120                 125
Ile Pro Glu Lys Lys Arg Lys Arg Ser Lys Tyr Lys Val Trp Ala Ser
     130                 135                 140
Tyr
145
```

( 2 ) INFORMATION FOR SEQ ID NO:2:

( i ) SEQUENCE CHARACTERISTICS:
        ( A ) LENGTH: 1123 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: PGANNOT01
        ( B ) CLONE: 620984

( x i ) SEQUENCE DESCRIPTION: SEQ ID NO:2:

```
TTGGGTCCGA CTGGAGCTCA GGCTCGCGAC CCAGACTGGT GGGCCAGGCC TCCAAGCCGG      60
CCTTACACCC AATCCAAGGA GGACAGACCG GACACAGAGG GACGGAGCGA GCAAGGAGAC     120
ATGGCTTCAT CATTCCTGCC CGCGGGGGCC ATCACCGGCG ACAGCGGTGG AGAGCTGAGC     180
TCAGGGGACG ACTCCGGGGA GGTGGAGTTC CCCCATAGCC CTGAGATCGA GGAGACCAGT     240
TGCCTGGCCG AGCTGTTTGA GAAGGCTGCC GCGCACCTGC AAGGCCTGAT TCAGGTGGCC     300
AGCAGGGAGC AGCTCTTGTA CCTGTATGCC AGGTACAAAC AGGTCAAAGT TGGAAATTGT     360
AATACTCCTA AACCAAGCTT CTTTGATTTT GAAGGAAAGC AAAAATGGGA AGCTTGGAAA     420
GCACTTGGTG ATTCAAGCCC CAGCCAAGCA ATGCAGGAAT ATATCGCAGT AGTTAAAAAA     480
CTAGATCCAG GTTGGAATCC TCAGATACCA GAGAAGAAAC GGAAAAGAAG CAAATACAAG     540
GTTTGGGCCA GTTATTAGTT CTCTATATCA TGAAGAAACC ATCAGGGAAG AGACAAAAAT     600
ATATTTGATT ACTGCAGGGA AACAACATT  GACCATATAA CCAAAGCCAT CAAATCGAAA     660
AATGTGGATG TGAATGTGAA AGATGAAGAG GGTAGGGCTC TACTTCACTG GGCCTGTGAT     720
CGAGGACATA AGGAACTAGT CACAGTGTTG CTGCAACATA GAGCTGACAT TAACTGTCAG     780
GACAATGAAG GCCAAACAGC TCTACATTAT GCCTCTGCCT GTGAGTTTCT GGATATTGTA     840
GAGCTGCTGC TCCAGTCTGG TGCTGACCCC ACTCTCCGAG ACCAGGATGG CTGCCTGCCA     900
GAGGAGGTGA CAGGCTGCAA AACAGTTTCT TTGGTGCTGC AGCGGCACAC AACTGGCAAG     960
GCTTAATCAA AAGACTGGAA AACTGCAGTC TGTAATAGCA TAAGGCTTCC ATTATGAAAG    1020
AAAACTACAA AAATAATACT TCTTTTCCAC CCGTCTTTGG TATGTATTGG CTAATAAAAT    1080
CAGTTCTGTG GAACTGGGAA AAAAAAAAA  AAAAAAAAA  AAA                     1123
```

( 2 ) INFORMATION FOR SEQ ID NO:3:

( i ) SEQUENCE CHARACTERISTICS:
        ( A ) LENGTH: 104 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 181478

( x i ) SEQUENCE DESCRIPTION: SEQ ID NO:3:

```
Met Trp Gly Asp Leu Trp Leu Leu Pro Pro Ala Ser Ala Asn Pro Gly
 1               5                  10                  15

Thr Gly Thr Glu Ala Glu Phe Glu Lys Ala Ala Glu Glu Val Arg His
            20                  25                  30

Leu Lys Thr Lys Pro Ser Asp Glu Glu Met Leu Phe Ile Tyr Gly His
        35                  40                  45

Tyr Lys Gln Ala Thr Val Gly Asp Ile Asn Thr Glu Arg Pro Gly Met
    50                  55                  60

Leu Asp Phe Thr Gly Lys Ala Lys Trp Asp Ala Trp Asn Glu Leu Lys
65                  70                  75                  80

Gly Thr Ser Lys Glu Asp Ala Met Lys Ala Tyr Ile Asn Lys Val Glu
                85                  90                  95

Glu Leu Lys Lys Lys Tyr Gly Ile
               100
```

( 2 ) INFORMATION FOR SEQ ID NO:4:

( i ) SEQUENCE CHARACTERISTICS:

(A) LENGTH: 86 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: GenBank
(B) CLONE: 118276

(xi) SEQUENCE DESCRIPTION: SEQ ID NO:4:

| Ser | Gln | Ala | Glu | Phe | Glu | Lys | Ala | Ala | Glu | Glu | Val | Arg | His | Leu | Lys |
|---|---|---|---|---|---|---|---|---|---|---|---|---|---|---|---|
| 1 | | | | 5 | | | | | 10 | | | | | 15 | |
| Thr | Lys | Pro | Ser | Asp | Glu | Glu | Met | Leu | Phe | Ile | Tyr | Gly | His | Tyr | Lys |
| | | | 20 | | | | 25 | | | | | | 30 | | |
| Gln | Ala | Thr | Val | Gly | Asp | Ile | Asn | Thr | Glu | Arg | Pro | Gly | Met | Leu | Asp |
| | | 35 | | | | | 40 | | | | | 45 | | | |
| Phe | Thr | Gly | Lys | Ala | Lys | Trp | Asp | Ala | Trp | Asn | Glu | Leu | Lys | Gly | Thr |
| | 50 | | | | | 55 | | | | | 60 | | | | |
| Ser | Lys | Glu | Asp | Ala | Met | Lys | Ala | Tyr | Ile | Asn | Lys | Val | Glu | Glu | Leu |
| 65 | | | | | 70 | | | | | 75 | | | | | 80 |
| Lys | Lys | Lys | Tyr | Gly | Ile | | | | | | | | | | |
| | | | | 85 | | | | | | | | | | | |

(2) INFORMATION FOR SEQ ID NO:5:

(i) SEQUENCE CHARACTERISTICS:
(A) LENGTH: 86 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: GenBank
(B) CLONE: 118275

(xi) SEQUENCE DESCRIPTION: SEQ ID NO:5:

| Ser | Gln | Ala | Glu | Phe | Asp | Lys | Ala | Ala | Glu | Glu | Val | Lys | His | Leu | Lys |
|---|---|---|---|---|---|---|---|---|---|---|---|---|---|---|---|
| 1 | | | | 5 | | | | | 10 | | | | | 15 | |
| Thr | Lys | Pro | Ala | Asp | Glu | Glu | Met | Leu | Phe | Ile | Tyr | Ser | His | Tyr | Lys |
| | | | 20 | | | | 25 | | | | | | 30 | | |
| Gln | Ala | Thr | Val | Gly | Asp | Ile | Asn | Thr | Glu | Arg | Pro | Gly | Met | Leu | Asp |
| | | 35 | | | | | 40 | | | | | 45 | | | |
| Phe | Lys | Gly | Lys | Ala | Lys | Trp | Asp | Ala | Trp | Asn | Glu | Leu | Lys | Gly | Thr |
| | 50 | | | | | 55 | | | | | 60 | | | | |
| Ser | Lys | Glu | Asp | Ala | Met | Lys | Ala | Tyr | Ile | Asp | Lys | Val | Glu | Glu | Leu |
| 65 | | | | | 70 | | | | | 75 | | | | | 80 |
| Lys | Lys | Lys | Tyr | Gly | Ile | | | | | | | | | | |
| | | | | 85 | | | | | | | | | | | |